US00PP21375P2

(12) United States Plant Patent
Lyrene

(10) Patent No.: US PP21,375 P2
(45) Date of Patent: Oct. 12, 2010

(54) SOUTHERN HIGHBUSH BLUEBERRY PLANT NAMED 'FL05-107'

(50) Latin Name: ***Vaccinium corymbosum* L.**
Varietal Denomination: FL05-107

(75) Inventor: Paul M. Lyrene, Micanopy, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/584,553

(22) Filed: Sep. 8, 2009

(51) Int. Cl.
*A01H 5/00* (2006.01)

(52) U.S. Cl. ..... Plt./157

(58) Field of Classification Search ..... Plt./157
See application file for complete search history.

*Primary Examiner*—Susan B McCormick Ewoldt
(74) *Attorney, Agent, or Firm*—Jondle & Associates, P.C.

(57) ABSTRACT

'FL05-107' is a new southern highbush blueberry plant distinguished by a low chilling requirement with prolific early-spring leafing, a vigorous, somewhat spreading plant habit, a 50% harvest date of about April 16 in northeast Florida and large, very firm berries with a good picking scar, is disclosed.

3 Drawing Sheets

STATEMENT REGARDING FEDERALLY SPONSORED RESEARCH

Figure 1:
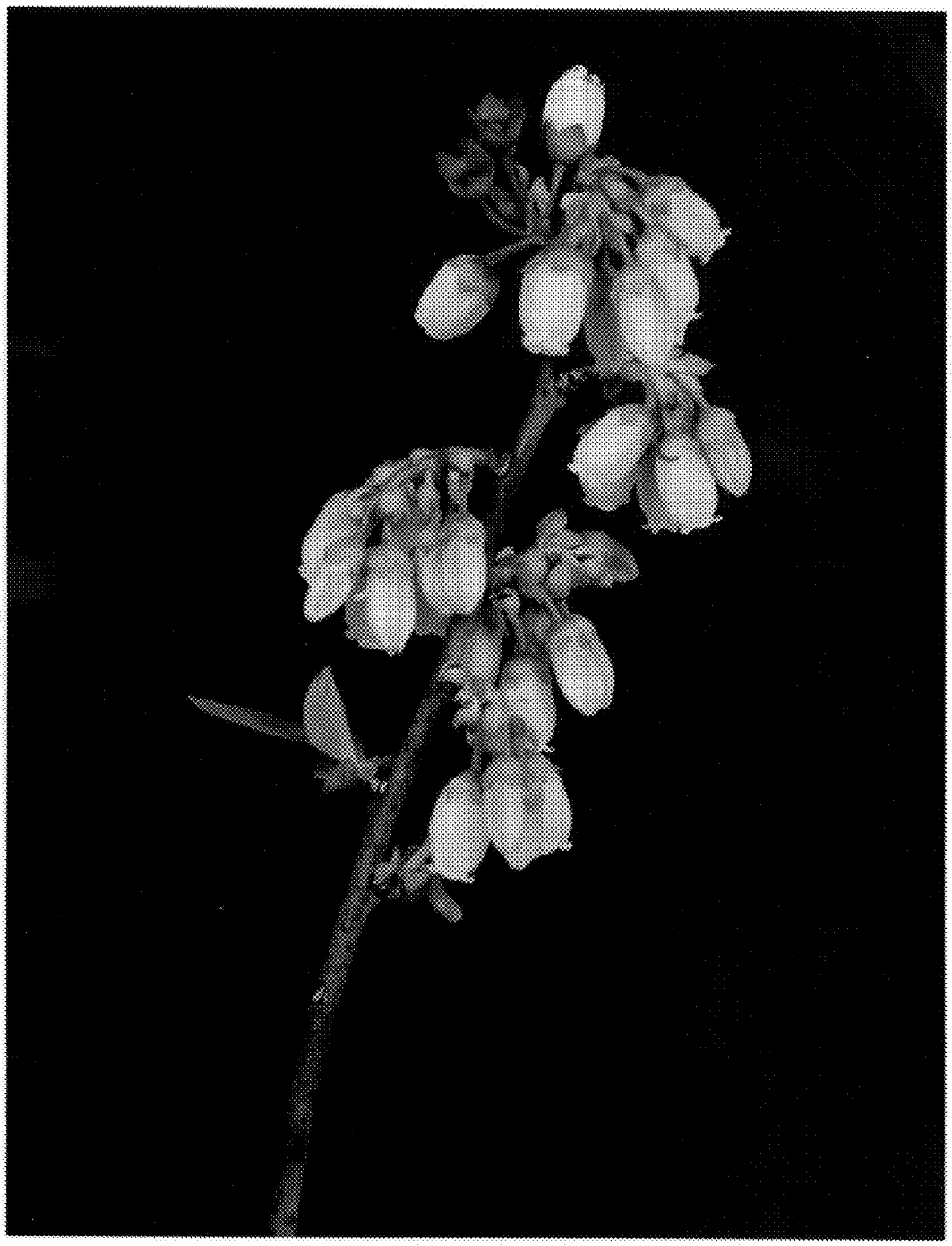

The present invention was supported in part by funds from the U.S. Government. The U.S. Government therefore may have certain rights in the invention.

Genus and species: *Vaccinium corymbosum* L.
Variety denomination:
'FL05-107'.

BACKGROUND OF THE INVENTION

The invention relates to a new and distinct variety of southern highbush blueberry (*Vaccinium corymbosum* L.) hybrid named 'FL05-107'. 'FL05-107' is intended for production of fresh-market blueberries in early spring from areas with mild winters and early spring warmth. 'FL05-107' is a southern highbush blueberry clone distinguished by its low chilling requirement, its vigorous, early-leafing bush, and by its large, firm berries that ripen from April 5 to May 1 when grown in north Florida. Several hundred plants of 'FL05-107' have been propagated by softwood cuttings at Gainesville, Fla., and the resulting plants have all been phenotypically indistinguishable from the original plant.

'FL05-107' originated as a seedling from the cross of the proprietary *Vaccinium corymbosum* L. female parent, 'FL02-13' (unpatented) and the proprietary *Vaccinium corymbosum* L. male parent, 'Farthing' (U.S. Plant Pat. No. 19,341) as part of the University of Florida breeding program in a greenhouse at Gainesville, Fla. in February of 2002. The seedling was first fruited in a high-density field nursery in April of 2004. After the second year of fruiting in the field, in the spring of 2005, 'FL05-107' was again propagated by softwood cuttings, and an experimental 15-plant test plot was established as part of a variety test in Windsor, Fla. in January of 2006. Based on the growth of the plants, the season of ripening, and the berry quality of this plot, 'FL05-107' was re-propagated by softwood cuttings in June of 2007 and an experimental 200-plant plot was established at Waldo, Fla. in January of 2008. Both the original and the subsequent test plantings were observed from flowering through fruit ripening in 2009, and no mutations or off-type plants were observed.

'FL05-107' has been reproduced asexually for over five years using softwood cuttings and has been found to retain its distinctive characteristics through successive asexual propagations.

Plant Breeder's Rights for this cultivar have not been applied for. 'FL05-107' has not been made publicly available more than one year prior to the filing date of this application.

SUMMARY OF THE INVENTION

The following are the most outstanding and distinguishing characteristics of 'FL05-107' when grown under normal horticultural practices in north Florida.

1. A low chilling requirement with prolific early-spring leafing;
2. A vigorous, somewhat spreading plant habit;
3. A 50% harvest date of about April 16 in northeast Florida; and
4. Large, very firm berries with a good picking scar.

DESCRIPTION OF THE PHOTOGRAPHS

This new southern highbush blueberry plant is illustrated by the accompanying photographs which show the plant's form, foliage, flower clusters and berry clusters. The colors shown are as true as can be reasonably obtained by conventional photographic procedures. The flowers that were photographed for FIG. 1 were taken from a 3-year-old plant grown in a field at Windsor, Fla. and were photographed in February of 2009. The berries photographed in FIG. 2 and FIG. 3 were from the same plant (as in FIG. 1) and were photographed in April of 2009.

FIG. 1 shows several clusters of opening flowers in February. The urceolate to cylindrical shape of the flower is visible. The unopened flowers have a rose-pink color, which is more intense in cold weather and bright sunlight, but the corollas are normally white by the time of anthesis.

Figure 2:
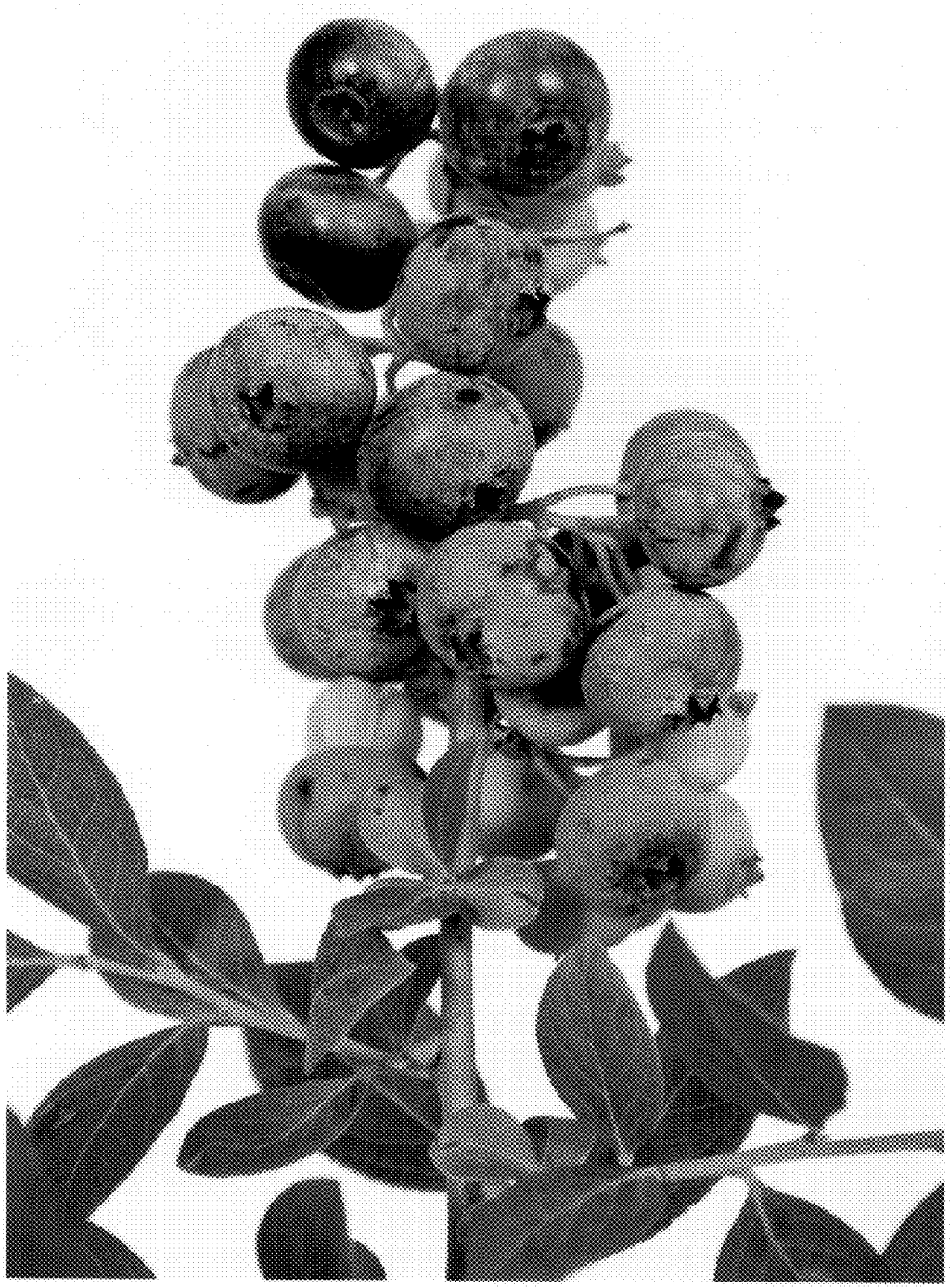

FIG. 2 shows several clusters of ripening berries. The freckling pattern is due to naturally occurring minerals in the water being used in overhead irrigation of the plants and is not an inherent feature of the berries. The loose berry clusters are visible.

Figure 3:
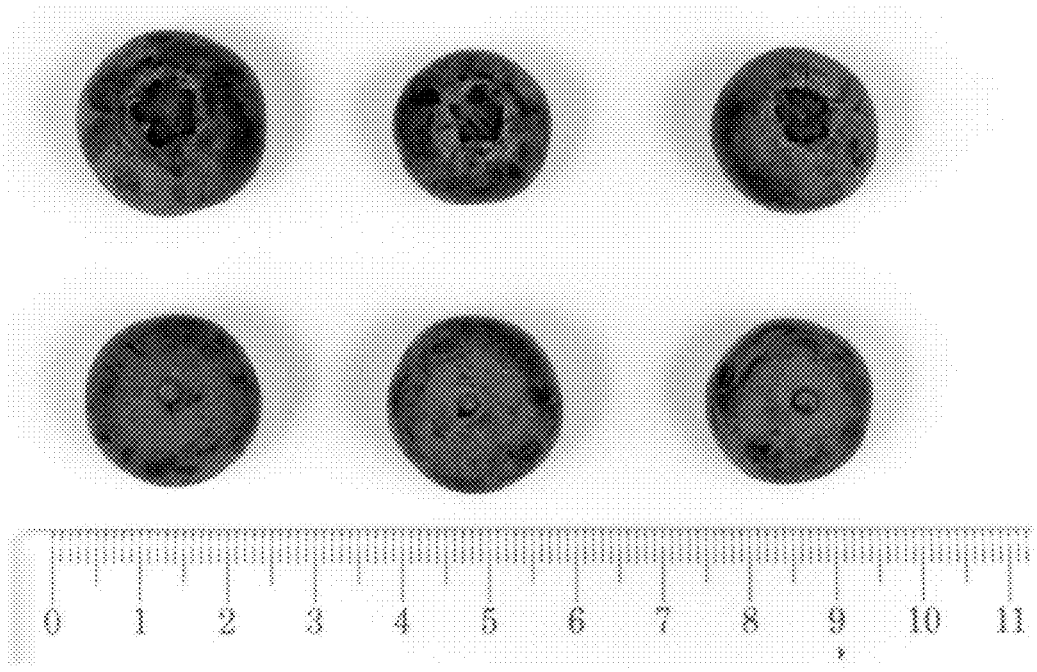

FIG. 3 shows berries at close range. The small, dry picking scars and the irregular calyx lobes, approximating a 5-point star on some berries, are visible.

DESCRIPTION OF THE NEW CULTIVAR

The following detailed description sets forth the distinctive characteristics of 'FL05-107.' The detailed description was taken on 3.5-year-old plants growing under field conditions near Windsor in northeast Florida. The descriptive data were taken between February and June of 2009, the date depending on the characteristic being measured. The color chart used in this specification is "The Pantone Book of Color", by Leatrice Eiseman and Lawrence Herbert. Harry N. Abrams, Inc., Publishers, N.Y. (1990). Where colors in the drawings differ from the Pantone color designations in the verbal descriptions, the Pantone color designations are accurate.

DETAILED BOTANICAL DESCRIPTION

Classification:

*Botanical name.*—*Vaccinium corymbosum* L.

*Common name.*—Southern highbush blueberry.

*Denomination.*—'FL05-107'.

Parentage:

*Female parent.*—'FL02-13' (unpatented).

*Male parent.*—'Farthing' (U.S. Plant Pat. No. 19,341).

*Market class.*—'FL05-107' produces southern highbush blueberries suitable for both the fresh and processed fruit markets.

Bush description:

*Plant height.*—1.5 m.

*Canopy diameter* (*measured at the widest part of the bush*).—2.0 m.

*Vigor.*—High.

*Growth habit.*—Somewhat spreading; produces a dense canopy.

*Twigginess.*—Low to medium.

*Tendency toward evergreenness.*—Medium.

*Productivity.*—In northeast Florida, 'FL05-107' produces 5 to 8 pounds of berries per bush on plants 3 years old or older.

*Chilling requirement.*—200 hours below 7° C.

*Cold hardiness.*—Flowers and fruit are hardy to −3° C.; during winter dormancy, the plant is hardy to −15° C.

*Ease of propagation.*—Easy to propagate from softwood cuttings; the plants survive and grow well in nursery beds.

Trunks and branches:

*Suckering tendency.*—Medium; 3.5-year-old plants have an average of 6 major canes rising from a crown 30 cm in diameter.

*Surface texture* (*of strong, 6-month-old shoots observed in June*).—Smooth.

*Surface texture* (*of 3-year-old and older wood*).—Rough due to exfoliation and production of vertical cracks.

*Color of 4-month-old twigs observed in June in the field.*—"Celery Green", Pantone 13-0532.

*Color of 3-year-old rough-textured canes.*—"Champaign Beige", Pantone 14-1012.

*Internode length on strong, upright shoots measured in June.*—Averages about 1.8 cm.

Leaves:

*Length, mean* (*including petiole, from tip of petiole to end of blade*).—5.7 cm.

*Width, mean* (*at widest point*).—2.5 cm.

*Shape.*—Ovate, terminating in a very short dew tip, 0.4 mm long, which is visible with a 15X microscope.

*Margin.*—Entire.

*Apex.*—Acute.

*Base.*—Acute.

*Color.*—Upper surface: "Chive", Pantone 19-0323. Lower surface: "Mistletoe", Pantone 16-0220.

*Pubescence.*—Upper surface: A few short, white hairs along the midrib. Lower surface: Absent.

*Pubescence on margins.*—Absent.

*Relative time of leafing versus flowering.*—In commercial fields in north Florida, where the variety is sprayed with hydrogen cyanamide in midwinter, the variety begins to produce new leaves at the time of full bloom.

Flower:

*Arrangement.*—Flowers are arranged alternately along a short, leafless, deciduous branch.

*Fragrance.*—Little to none.

*Shape.*—Urceolate to cylindrical.

*Flowering period.*—Mean date of 50% open flowers in Windsor, Fla. is February 3.

*Cluster habit.*—Loose.

*Median number of flowers per cluster.*—6.

*Petals.*—Fused into a corolla with 5 lobes.

*Pedicel.*—Length at time of anthesis: 0.8 cm. Color: "Red Violet", Pantone 17-1818 on the side exposed to the sun.

*Peduncle.*—Length at time of anthesis: Highly variable; median is 1.0 cm. Color: "Red Violet", Pantone 17-1818 on the side exposed to the sun.

*Calyx.*—Surface texture: Smooth. Color at anthesis: "Herbal Green", Pantone 15-0336.

*Corolla.*—Length (from pedicel attachment to corolla tip excluding the pedicel): 1.0 cm. Diameter of tube (at widest point): 0.6 cm. Aperture diameter: 0.3 cm. Surface texture: Smooth. Color at anthesis: White.

Reproductive organs:

*Style length* (*top of ovary to stigma tip*).—0.9 cm.

*Location of tip of stigma relative to lip of the corolla.*—Co-equal.

*Pollen.*—General: When the pollen is stained with 2% acetocarmine, the potential pollen fertility can be measured; 98% of the pollen tetrads stain well and appear to be well developed. Abundance of shed: Very high. Color of dried pollen: "Winter White", Pantone 11-0507.

Self-fruitfulness: Low to medium; planting in field configurations that promote cross pollination with other southern highbush clones is recommended for all southern highbush in Florida.

Fruit:

*Mean date of first commercial harvest* (*25% of berries ripe*).—April 8.

*Mean date of mid-harvest.*—April 16.

*Mean date of last harvest.*—May 1.

*Size and shape of calyx lobes on mature berry.*—Irregular; on some berries the lobes form a 5-point star.

*Pedicel length on ripe berry.*—Median is 0.6 cm.

*Peduncle length on ripe berry.*—Variable; median is 1.2 cm.

*Detachment force for ripe berries.*—Very easily detached.

*Number of berries per cluster.*—Median is 5.

Berry:

*Cluster habit.*—Loose.

*Weight* (*on well-pruned plants*).—2.6 g per berry.

*Height.*—1.4 cm.

*Width.*—1.9 cm.

*Diameter of calyx aperture on mature berry* (*longest diameter*).—0.6 cm.

*Shape.*—Subglobose; the polar diameter is shorter than the equatorial diameter.

*Surface color of immature berries, with bloom.*—"Ice", Pantone 11-4803.

*Surface color of mature berries while on the plant.*—"Lilac Gray", Pantone 14-3903.

*Surface color of ripe berry after polishing.*—Shiny black.

*Surface wax.*—Slightly less than medium in amount and in persistence during handling of the berry.

*Pedicel scar.*—Small and dry.

*Firmness.*—High.

*Flavor.*—Quite acid (tart) when first blue; becoming sweeter if allowed to hang on the plant for several days after the color change.

*Texture.*—Good; small seeds, thin skin.

Seeds:

*Color of dried seeds.*—"Bran", Pantone 17-1336.

*Weight of well-developed dried seed.*—0.5 mg per seed.

*Length of well-developed dried seed.*—Mean is 0.2 cm.

Disease and insect resistance: 'FL05-107' has grown vigorously and shows medium to good bush survival in the field. 'FL05-107' appears to have above-average resistance to root rot (*Phytophthora cinnamomi*) and stem blight (*Botryosphaeria* spp.). The fungal leaf spots that are common on highbush blueberries grown in Florida are easily controlled by approved fungicides.

COMPARISON WITH PARENTAL LINES AND KNOWN CULTIVARS

'FL05-107' is distinguished from the proprietary *Vaccinium corymbosum* L. female parent, 'FL02-13' (unpatented) in that 'FL05-107' has a larger berry and a better plant survival than 'FL02-13.'

'FL05-107' is distinguished from the proprietary *Vaccinium corymbosum* L. male parent, 'Farthing' (U.S. Plant Pat. No. 19,341) in that 'FL05-107' has a larger, more open growth habit, larger berries, and has berries than ripen approximately one week earlier than 'Farthing.'

'FL05-107' is distinguished from the comparison commercial variety 'Primadonna' (U.S. Plant Pat. No. 20,181) in that 'FL05-107' has ovate shaped leaves and a median number of 6 flowers per cluster, while 'Primadonna' has elliptical shaped leaves and a median number of 7 flowers per cluster.

'FL05-107' is distinguished from the comparison commercial variety 'Star' (U.S. Plant Pat. No. 10,675) in that 'FL05-107' has berries that ripen approximately 1 week earlier than 'Star.' 'FL05-107' has a more vigorous growth habit and has an earlier flowering period (the mean date of 50% open flower at Windsor, Fla. is on average, 5 to 15 days before 'Star').

I claim:

1. A new and distinct cultivar of southern highbush blueberry plant as shown and described herein.

* * * * *